(12) United States Patent
Hansen et al.

(10) Patent No.: US 9,265,893 B2
(45) Date of Patent: Feb. 23, 2016

(54) INJECTION BUTTON

(75) Inventors: Torben Stroem Hansen, Copenhagen V (DK); Jakob Oest Wielandt, Copenhagen N (DK); Lars Moerch Groth, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 1707 days.

(21) Appl. No.: 12/525,976

(22) PCT Filed: Jan. 21, 2008

(86) PCT No.: PCT/EP2008/050624
§ 371 (c)(1),
(2), (4) Date: Dec. 16, 2009

(87) PCT Pub. No.: WO2008/095762
PCT Pub. Date: Aug. 14, 2008

(65) Prior Publication Data
US 2010/0145282 A1    Jun. 10, 2010

Related U.S. Application Data

(60) Provisional application No. 60/899,977, filed on Feb. 7, 2007.

(30) Foreign Application Priority Data

Feb. 5, 2007   (EP) ..................................... 07101729

(51) Int. Cl.
*A61M 5/00*   (2006.01)
*A61M 5/315*   (2006.01)

(52) U.S. Cl.
CPC ....... *A61M 5/31585* (2013.01); *A61M 5/31511* (2013.01); *A61M 5/3158* (2013.01)

(58) Field of Classification Search
CPC ................. A61M 2005/2013; A61M 5/31541; A61M 5/20; A61M 5/31583; A61M 5/3158
USPC .................................. 604/181, 187, 218–231
See application file for complete search history.

(56) References Cited

U.S. PATENT DOCUMENTS 2,444,570 A    8/1946    Lawrence et al.
4,470,317 A    9/1984    Sabloewski et al.
(Continued)

FOREIGN PATENT DOCUMENTS

DE    3609555 A1    9/1987
EP    295075    12/1988
(Continued)

OTHER PUBLICATIONS

U.S. Appl. No. 10/960,900, filed Oct. 7, 2004, Steedfeldt-Jensen.
(Continued)

*Primary Examiner* — Phillip Gray
(74) *Attorney, Agent, or Firm* — Wesley Nicolas

(57) ABSTRACT

A push button connection for an injection device comprising a push button (10) and a driving part (20). The two parts of the push button connection are mounted to each other and is relatively rotatable to each other. In order to minimize the friction occurring between the push button and the driving part when relatively rotated forces are transmitted via a pivot bearing (18, 22). In order also to minimize the effect of forces appearing dislocated from the center line a number of radial bearings (13, 23; 14, 25) having a little friction diameter is provided.

6 Claims, 2 Drawing Sheets

(56) References Cited

U.S. PATENT DOCUMENTS

| | | |
|---|---|---|
| 4,498,904 A | 2/1985 | Turner et al. |
| 4,568,335 A | 2/1986 | Updike et al. |
| 4,585,439 A | 4/1986 | Michel |
| 4,592,745 A | 6/1986 | Rex et al. |
| 4,833,379 A | 5/1989 | Kaibel et al. |
| 4,865,591 A | 9/1989 | Sams |
| 4,883,472 A | 11/1989 | Michel |
| 4,919,596 A | 4/1990 | Slate et al. |
| 4,936,833 A | 6/1990 | Sams |
| 4,973,318 A | 11/1990 | Holm et al. |
| 4,994,033 A | 2/1991 | Shockey et al. |
| 5,017,190 A | 5/1991 | Simon et al. |
| 5,092,842 A | 3/1992 | Bechtold et al. |
| 5,112,317 A | 5/1992 | Michel |
| 5,207,752 A | 5/1993 | Sorenson et al. |
| 5,226,895 A | 7/1993 | Harris |
| 5,246,417 A | 9/1993 | Haak et al. |
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,284,480 A | 2/1994 | Porter et al. |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,370,629 A | 12/1994 | Michel et al. |
| 5,380,297 A | 1/1995 | Wadman et al. |
| 5,383,166 A * | 1/1995 | Gallay ............... G04B 37/103 368/288 |
| 5,383,865 A | 1/1995 | Michel |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,480,387 A | 1/1996 | Gabriel et al. |
| 5,492,534 A | 2/1996 | Athayde et al. |
| 5,505,704 A | 4/1996 | Pawelka et al. |
| 5,545,147 A | 8/1996 | Harris |
| 5,546,932 A | 8/1996 | Galli |
| 5,549,574 A | 8/1996 | Townsend |
| 5,549,575 A | 8/1996 | Giambattista et al. |
| 5,584,815 A | 12/1996 | Pawelka et al. |
| 5,591,136 A | 1/1997 | Gabriel |
| 5,599,314 A | 2/1997 | Neill |
| 5,611,783 A | 3/1997 | Mikkelsen |
| 5,626,566 A | 5/1997 | Petersen et al. |
| 5,645,052 A | 7/1997 | Kersey |
| 5,674,204 A | 10/1997 | Chanoch |
| 5,679,111 A | 10/1997 | Hjertman et al. |
| 5,681,285 A | 10/1997 | Ford et al. |
| 5,685,864 A | 11/1997 | Shanley et al. |
| 5,688,251 A | 11/1997 | Chanoch |
| 5,693,027 A | 12/1997 | Hansen et al. |
| 5,709,662 A | 1/1998 | Olive et al. |
| 5,716,990 A | 2/1998 | Bagshawe et al. |
| 5,725,508 A | 3/1998 | Chanoch |
| 5,743,889 A | 4/1998 | Sams |
| 5,755,692 A | 5/1998 | Manicom |
| 5,823,998 A | 10/1998 | Yamagata |
| 5,827,232 A | 10/1998 | Chanoch et al. |
| 5,843,036 A | 12/1998 | Olive et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,938,642 A | 8/1999 | Burroughs et al. |
| 5,947,934 A | 9/1999 | Hansen et al. |
| 5,951,530 A | 9/1999 | Steengaard et al. |
| 5,954,689 A | 9/1999 | Poulsen |
| 5,961,496 A | 10/1999 | Nielsen et al. |
| 5,980,491 A | 11/1999 | Hansen |
| 5,984,900 A | 11/1999 | Mikkelsen |
| 6,003,736 A | 12/1999 | Ljunggren |
| 6,004,297 A | 12/1999 | Steenfeldt-Jensen et al. |
| 6,010,485 A | 1/2000 | Buch-Rasmussen et al. |
| 6,033,376 A | 3/2000 | Rockley |
| 6,033,377 A | 3/2000 | Rasmussen et al. |
| 6,048,336 A | 4/2000 | Gabriel |
| 6,074,372 A | 6/2000 | Hansen |
| 6,083,197 A | 7/2000 | Umbaugh |
| 6,086,567 A | 7/2000 | Kirchhofer et al. |
| 6,096,010 A | 8/2000 | Walters et al. |
| 6,110,149 A | 8/2000 | Klitgaard et al. |
| 6,129,080 A | 10/2000 | Pitcher et al. |
| 6,146,361 A | 11/2000 | DiBiasi et al. |
| 6,193,698 B1 | 2/2001 | Kirchhofer et al. |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 | 5/2001 | Steenfeldt-Jensen et al. |
| 6,248,090 B1 | 6/2001 | Jensen et al. |
| 6,248,095 B1 | 6/2001 | Giambattista et al. |
| 6,258,062 B1 | 7/2001 | Thielen et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen et al. |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,379,339 B1 | 4/2002 | Klitgaard et al. |
| 6,514,230 B1 | 2/2003 | Munk et al. |
| 6,547,763 B2 | 4/2003 | Steenfeldt-Jensen et al. |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,605,067 B1 | 8/2003 | Larsen |
| 6,613,019 B2 | 9/2003 | Munk |
| 6,663,602 B2 | 12/2003 | Moller |
| 6,692,472 B2 | 2/2004 | Hansen et al. |
| 6,716,198 B2 | 4/2004 | Larsen |
| 6,726,661 B2 | 4/2004 | Munk et al. |
| 6,770,288 B2 | 8/2004 | Duirs |
| 6,796,970 B1 | 9/2004 | Klitmose et al. |
| 6,893,415 B2 | 5/2005 | Madsen et al. |
| 6,899,698 B2 | 5/2005 | Sams |
| 6,899,699 B2 | 5/2005 | Enggaard |
| 6,945,961 B2 | 9/2005 | Miller et al. |
| 7,008,399 B2 | 3/2006 | Larsen et al. |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,112,187 B2 | 9/2006 | Karlsson |
| 7,133,329 B2 | 11/2006 | Skyggebjerg et al. |
| 7,175,055 B2 | 2/2007 | Hansen et al. |
| RE43,834 E | 11/2012 | Steenfeldt-Jensen et al. |
| 2002/0007154 A1 | 1/2002 | Hansen et al. |
| 2002/0052578 A1 | 5/2002 | Moller |
| 2002/0077852 A1 | 6/2002 | Ford et al. |
| 2002/0120235 A1 | 8/2002 | Enggaard |
| 2003/0039679 A1 | 2/2003 | Duirs |
| 2003/0172924 A1 | 9/2003 | Staniforth et al. |
| 2004/0059299 A1 | 3/2004 | Moller |
| 2004/0186431 A1 | 9/2004 | Graf et al. |
| 2004/0210199 A1 | 10/2004 | Atterbury et al. |
| 2004/0236282 A1 | 11/2004 | Braithwaite |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2005/0004529 A1 | 1/2005 | Veasey et al. |
| 2005/0019400 A1 | 1/2005 | Deveney et al. |
| 2005/0033244 A1 | 2/2005 | Veasey et al. |
| 2005/0055011 A1 | 3/2005 | Enggaard |
| 2005/0205083 A1 | 9/2005 | Staniforth et al. |

(56) References Cited

U.S. PATENT DOCUMENTS

| | | |
|---|---|---|
| 2005/0268915 A1 | 12/2005 | Wassenaar et al. |
| 2007/0093761 A1 | 4/2007 | Veasey et al. |

FOREIGN PATENT DOCUMENTS

| | | |
|---|---|---|
| EP | 327910 | 8/1989 |
| EP | 359070 A2 | 3/1990 |
| EP | 450905 A1 | 10/1991 |
| EP | 0452281 A1 | 10/1991 |
| EP | 498737 | 8/1992 |
| EP | 879610 | 8/1992 |
| EP | 608343 | 4/1993 |
| EP | 554996 | 8/1993 |
| EP | 594349 | 4/1994 |
| EP | 0673482 | 9/1995 |
| EP | 702970 | 3/1996 |
| EP | 0937471 | 8/1999 |
| EP | 937476 | 8/1999 |
| EP | 1003581 | 8/1999 |
| EP | 1250167 A1 | 10/2002 |
| EP | 1570876 A2 | 9/2005 |
| FR | 2583291 | 12/1986 |
| FR | 2767479 | 2/1999 |
| GB | 735443 A | 8/1955 |
| GB | 995065 A | 6/1965 |
| GB | 1232899 A | 5/1971 |
| GB | 2141799 A | 1/1985 |
| HU | 213691 B | 9/1997 |
| HU | 215007 B | 8/1998 |
| HU | 215366 B | 12/1998 |
| HU | 215634 B | 1/1999 |
| JP | 05-337179 | 12/1993 |
| JP | 06-296691 | 10/1994 |
| JP | 2002501790 A | 1/2002 |
| RU | 2111019 | 5/1997 |
| TW | 267945 B | 1/1996 |
| WO | 8907463 | 8/1989 |
| WO | 90/09202 | 8/1990 |
| WO | 9110460 A1 | 7/1991 |
| WO | 91/14467 A1 | 10/1991 |
| WO | 93/07922 | 4/1993 |
| WO | 94/19034 A1 | 9/1994 |
| WO | 9626754 | 9/1996 |
| WO | 9638190 | 12/1996 |
| WO | 9736626 | 10/1997 |
| WO | 9810813 | 3/1998 |
| WO | 9856436 | 12/1998 |
| WO | 9857688 | 12/1998 |
| WO | 9916487 | 4/1999 |
| WO | 9938554 | 8/1999 |
| WO | 01/19434 A1 | 3/2001 |
| WO | 2005018721 | 3/2005 |

OTHER PUBLICATIONS

U.S. Appl. No. 11/121,331, filed May 3, 2005, Steedfeldt-Jensen.
U.S. Appl. No. 11/640,610, filed Dec. 18, 2006, Steedfeldt-Jensen.

* cited by examiner

INJECTION BUTTON

CROSS-REFERENCE TO RELATED APPLICATIONS

This application is a 35 U.S.C. §371 national stage application of International Patent Application PCT/EP2008/050624 (published as WO2008/095762), filed Jan. 21, 2008, which claimed priority of European Patent Application 07101729.7, filed Feb. 5, 2007; this application further claims priority under 35 U.S.C. §119 of U.S. Provisional Application 60/899,977, filed Feb. 7, 2007.

THE TECHNICAL FIELD OF THE INVENTION

The invention relates to a push button connection for an injection device and especially to such connection where a push button is rotated relatively to a driving member to which it is connected.

DESCRIPTION OF RELATED ART

U.S. Pat. No. 6,235,004 discloses an injection device in which according to FIG. 15-16 a dose is set by rotating the scale drum out of the housing in a threaded connection. When injecting the set dose the user pushes on the push button which forces the scale drum and the bushing to rotate together back into the housing. During this rotation of the bushing to which the push button is attached, the push button and the bushing rotates relatively to each other. The friction occurring between these relatively rotatable parts contributes to the force a user needs to apply in order to push back the bushing and the scale drum in order to inject the set dose.

U.S. Pat. No. 7,427,275 discloses an injection device in which the push button is formed with a bore encompassing a stem on a sleeve member. The push button and the stem are welded together such that the push button and the sleeve member are axially and rotatably fixed to each other.

DESCRIPTION OF THE INVENTION

It is an object of the present invention to provide a dose button connection for an injection device which minimizes the forces a user must apply to inject a dose.

When a user pushes on the injection button, the force applied is directed to the forward movement of the driving part, however, since the push button and the driving part rotate relatively to each other a friction between these rotating parts will occur. The user therefore also has to apply a force large enough to overcome this friction. One way of minimizing the force a user must apply in order to perform an injection is therefore to minimize this friction. By forming a pivot bearing between the two parts, the surface area of interaction between the two objects can be minimized and the radius of the resulting friction force can be kept at a minimum.

In order to secure the fit between the push button and the driving part and on the same time direct forces applied on the periphery of the push button to the driving part at least one radial bearing between the push button and the protrusion is formed.

Preferably one radial bearing is formed in the upper area and one is formed in the lower area both having the least possible radius of friction. In this way forces applied at in the periphery area of the push button and causing tilting of the push button on the protrusion of the driving part is properly transferred.

If a user applies a force eccentric to the centre axis of the push button i.e. on a peripheral area of the button, the push button will tilt and a reaction torque will occur at the radial bearings. In order to minimize this force pair, which in this load case is located at the distance from the radial bearing surface to the centre axis of the system, this distance, which again equals the radius of the protrusion, must be as little as possible and the distance between the bearings as long as possible. However, in order not to make the protrusion too narrow and fragile it is preferred to balance the radius of the bearings, such that the upper bearing has the smallest diameter and the lower bearing at the root of the column shaped protrusion has a diameter large enough to resist the bending force as a result of the offset applied push button forces.

In order to assemble the push button in an irreversible manner making it difficult to dissemble, it is preferred to secure the push button at the intended position by adding a track into which a rim on the harder part is forced during the manufacture of the injection device. The necessary compliance of the push button for the assembly snap-on can be secured by selection of a soft material and/or a vertical slit in the hollow section of the geometry.

Further the materials used for the push button and the protrusion on the driving part could be materials having low internal friction, or the materials could be surface treated in order to lower the internal friction.

The push button used in the connection has a central bore dedicated to engage the protrusion provided on the driving part. The bottom of the bore is preferable formed with a pivot. This pivot bears on a surface of the protrusion thus forming a pivot bearing.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
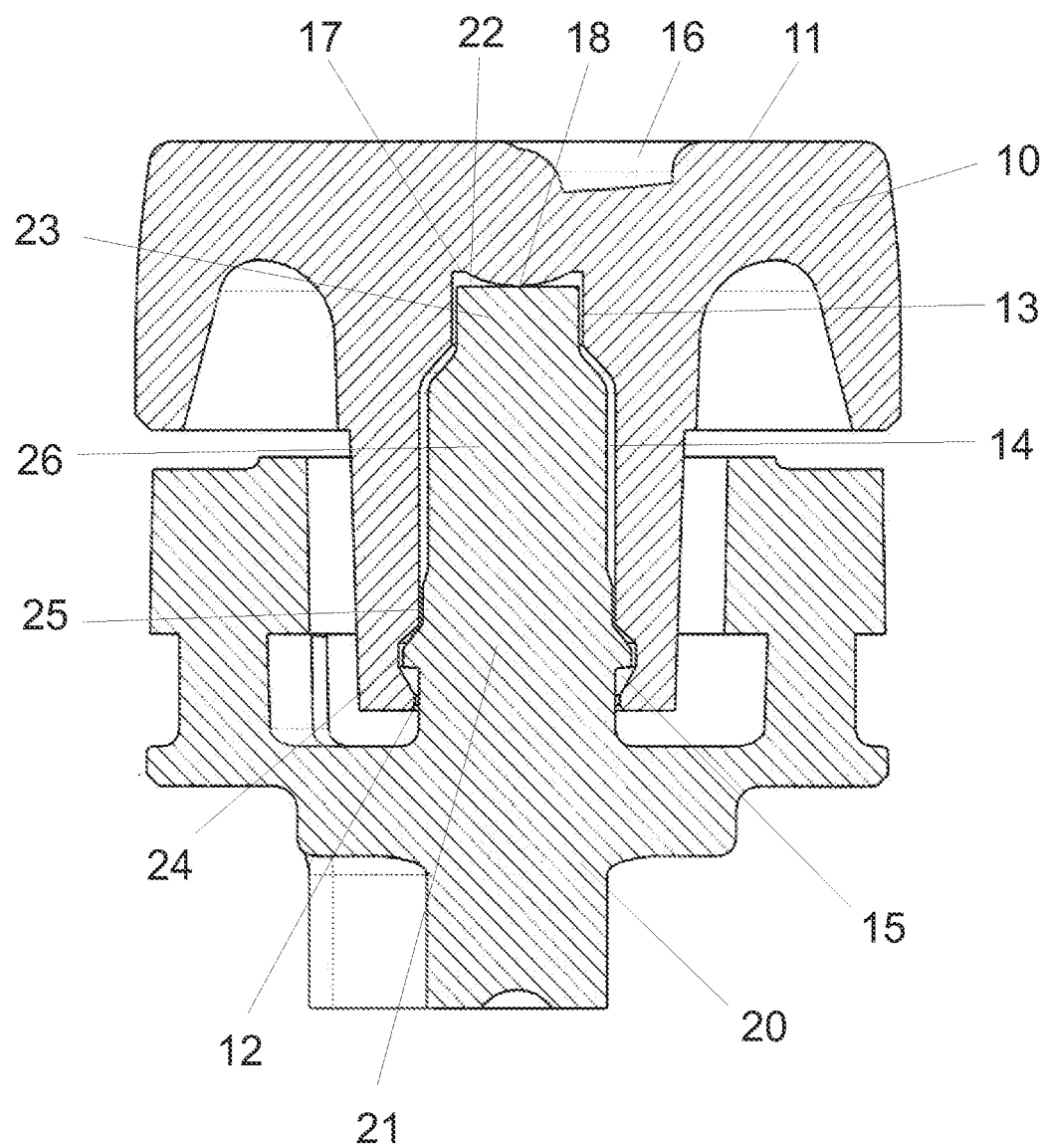
FIG. 1 Show a cross section view of the connection between a push button and a driving part.

FIG. 1 discloses the connection between the push button 10 and the driving part 20.

When a user wants to inject a dose, which he or she has first selected, the user pushes the push button 10 which then moves the driving part 20 axially forward in the injection device. During this forward movement of the driving part 20 it also rotates usually because it is interfaced with a dose dial drum which is threadedly connected to a housing. Such injection device is described in details in EP 1.003.581. The combined axial and rotatable movement of the driving part 20 drives the set dose out from the injection device.

As the users finger pushes on the push surface 11 of the push button 10 it is unable to rotate due to the friction between the users finger and the push button 10 whereas the driving part 20 is forced to rotate due to its interface, therefore a relative rotation between the push button 10 and the driving part 20 takes place.

The push button 10 which could be manufactured from a suitable polymeric material being softer that the material from which the driving part 20 is manufactured comprises at the proximal end a push surface 11 which is contacted by the user's finger when a dose is to be injected and an opposite located cylindrical bore 12 with a circular cross section. The most proximal part 13 of the bore 12 has a smaller diameter than the remaining part 14 of the bore 12. At the distal end of the bore 12, a radial extending track 15 is provided.

The push surface 11 could be provided with a tactile cut-out 16 informing visual impaired users on the content of the injection device and the most proximal bottom surface 17 of the bore 12 is formed with a raised pointer forming a pivot 18.

The driving part 20 is provided with a protrusion 21 having a circular cross section and a top surface 22. This protrusion 21 has at its proximal end a top part 23 with a decreased diameter compared to the remaining part 26 of the protrusion 21. Further the protrusion 21 is provided with a radial extending rim 24 at its distal end. In the area around this rim 24, the protrusion 21 is provided with a belt 25 with a slightly raised diameter.

When the push button 10 is mounted on the protrusion 21 of the driving element 20 it is simply clicked on such that the extending rim 24 enters the track 15. This forms a connection almost impossible to disconnect since the polymeric material of the push button 10 is softer than the material from which the protrusion 21 is produced. In this position the pivot 18 formed in the most proximal bottom surface 17 of the bore 12 bears on the top surface 22 of the protrusion 21 thus forming a pivot bearing 22, 18. Further the push button 10 is radially supported by the protrusion 21 at the top part 23 forming a radial top bearing 23, 13. The belt 25 on the protrusion 21 bears on an area of the remaining part 14 of the bore 12 thus forming a radial bottom bearing 14, 25.

Figure 2:
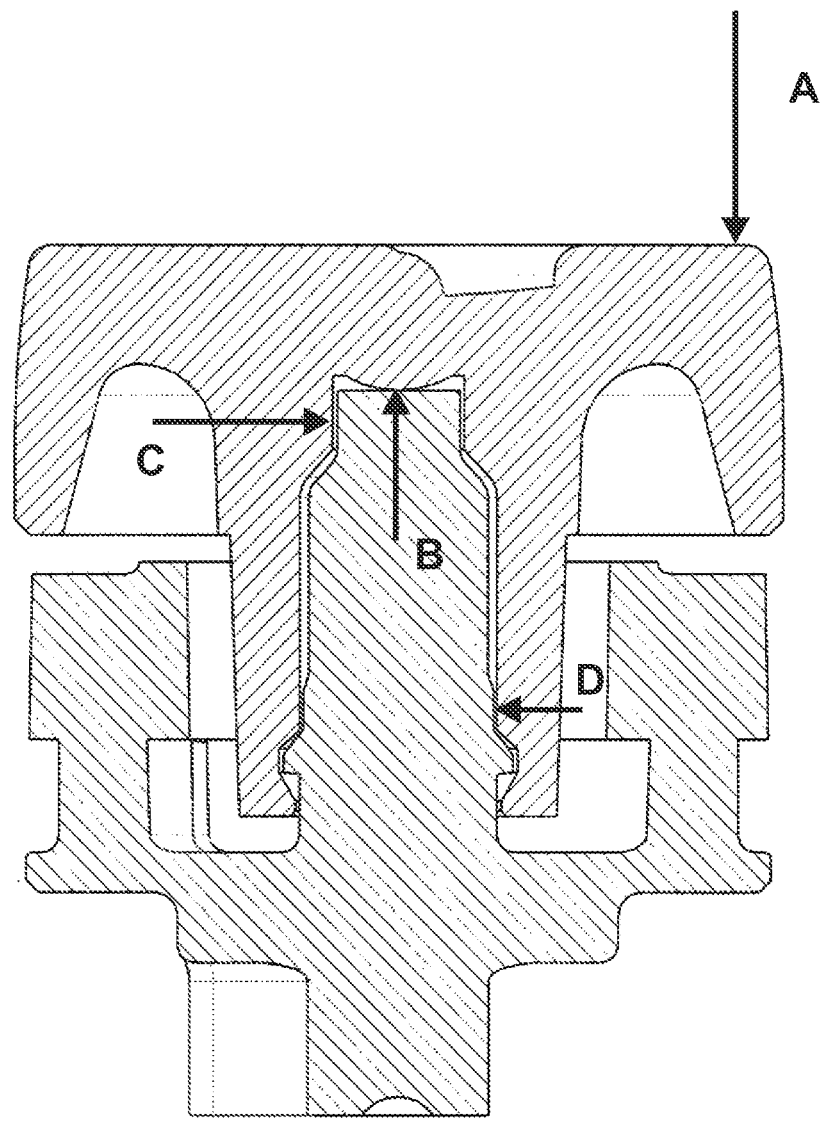
FIG. 2 Show a cross section view of the connection and the forces occurring.

In FIG. 2 the push button 10 connection is disclosed with the various forces occurring when a user applies an injection force in the peripheral area of the push button 10.

When the user applies an injection force A at the peripheral area of the push button 10 a vertical reaction force B will appear at the pivot point 22, 18, at the same time a radial force C will occur at the upper radial bearing 13, 23. Since the upper radial bearing 13, 23 are located at the top part 23 having the smaller diameter, the resulting torque is relatively small. Further, a radial force D will occur at the lower radial bearing 14, 25, however due to the distance between the upper radial bearing 13, 23 and the lower radial bearing 14, 25, the force resulting on the lower radial bearing 14, 25 is relatively small.

Some preferred embodiments have been shown in the foregoing, but it should be stressed that the invention is not limited to these, but may be embodied in other ways within the subject matter defined in the following claims.

The invention claimed is:

1. A push button connection for an injection device comprising:
    a push button mountable on a driving part being rotatable relatively to the push button and which push button further comprises a bore with a bottom surface and which bore surrounds a protrusion on the driving part which protrusion has a top surface and wherein a pivot bearing is formed between the bottom surface and the top surface, wherein when a user presses on the push button the force is directed toward the driving part and wherein the driving part rotates relative to the push button.

2. A push button connection according to claim 1, in which at least one radial bearing between the push button and the driving part is provided.

3. A push button connection according to claim 2, in which an upper radial bearing is provided at a top part of the protrusion and a lower radial bearing is provided at the bottom of the protrusion.

4. A push button connection according to claim 3, in which the top part of the protrusion accommodating the upper radial bearing has a diameter smaller than the diameter of the remaining part of the protrusion.

5. A push button connection according to claim 1, in which the push button is manufactured from a polymeric material being softer than the material from which the driving part is manufactured.

6. A push button connection according to claim 1, in which the protrusion is provided with an extending rim mating with a track provided in the push button.

* * * * *